US008720438B2

(12) United States Patent
Hecox et al.

(10) Patent No.: US 8,720,438 B2
(45) Date of Patent: May 13, 2014

(54) BREATHING MASK WITH STICKY EDGE

(75) Inventors: Lawrence E. Hecox, Ventura, CA (US);
David Eckhous, Long Beach, CA (US);
Blain Tomlinson, Long Beach, CA (US)

(73) Assignee: CPaiR, Inc., Ventura, CA (US)

( * ) Notice: Subject to any disclaimer, the term of this patent is extended or adjusted under 35 U.S.C. 154(b) by 1064 days.

(21) Appl. No.: 12/328,665

(22) Filed: Dec. 4, 2008

(65) Prior Publication Data

US 2009/0145430 A1 Jun. 11, 2009

Related U.S. Application Data

(60) Provisional application No. 60/992,863, filed on Dec. 6, 2007.

(51) Int. Cl.
*A61M 16/00* (2006.01)
*A61M 15/00* (2006.01)
*A62B 7/00* (2006.01)
*A62B 18/08* (2006.01)

(52) U.S. Cl.
USPC ............ 128/202.28; 128/202.18; 128/206.24; 128/206.29

(58) Field of Classification Search
USPC ............ 128/206.21, 206.23, 206.25, 206.28, 128/200.26, 201.21–201.23, 201.26, 128/202.16, 202.18, 202.28–202.29, 128/203.11, 204.18, 206.24, 206.29; 362/103, 105, 372
See application file for complete search history.

(56) References Cited

U.S. PATENT DOCUMENTS

| | | | | |
|---|---|---|---|---|
| 4,247,961 A | * | 2/1981 | Masch et al. | 5/639 |
| 4,559,940 A | * | 12/1985 | McGinnis | 128/206.26 |
| 4,574,338 A | * | 3/1986 | Takasaki et al. | 362/278 |
| 5,269,035 A | * | 12/1993 | Hartunian | 5/638 |
| 5,357,642 A | * | 10/1994 | Clute | 5/655 |
| 5,592,938 A | | 1/1997 | Scarberry | |
| 5,709,649 A | * | 1/1998 | Chitwood | 602/32 |
| 6,082,360 A | | 7/2000 | Rudolph | |
| 6,196,223 B1 | | 3/2001 | Belfer | |
| 6,446,288 B1 | | 9/2002 | Pi | |
| 6,526,967 B2 | | 3/2003 | Cordero et al. | |
| 6,851,429 B2 | | 2/2005 | Bishop | |
| 6,895,965 B2 | | 5/2005 | Scarberry | |
| 7,178,931 B1 | * | 2/2007 | Murphy | 362/105 |
| 7,293,990 B2 | | 11/2007 | Hirsch | |
| 2003/0062040 A1 | | 4/2003 | Lurie | |
| 2005/0056286 A1 | | 3/2005 | Huddart | |
| 2005/0234526 A1 | * | 10/2005 | Gilhuly et al. | 607/86 |

FOREIGN PATENT DOCUMENTS

| | | |
|---|---|---|
| CA | 2604491 | 10/2005 |
| GB | 2215216 | 9/1989 |

* cited by examiner

*Primary Examiner* — Tan-Uyen T. Ho
*Assistant Examiner* — Mark K Han
(74) *Attorney, Agent, or Firm* — Fish & Tsang LLP

(57) ABSTRACT

Breathing assist kits having a cranio-cervical extension device and a strapless breathing mask are presented. The mask comprises a seal that couples the mask to a victim's face preferably using an adhesive gasket that ensures the mask does not become dislodged while a care giver provides assisted breathing. The mask can also include, among other enhancements, a window or a light gathering lens to provide a view into the victim's mouth.

10 Claims, 2 Drawing Sheets

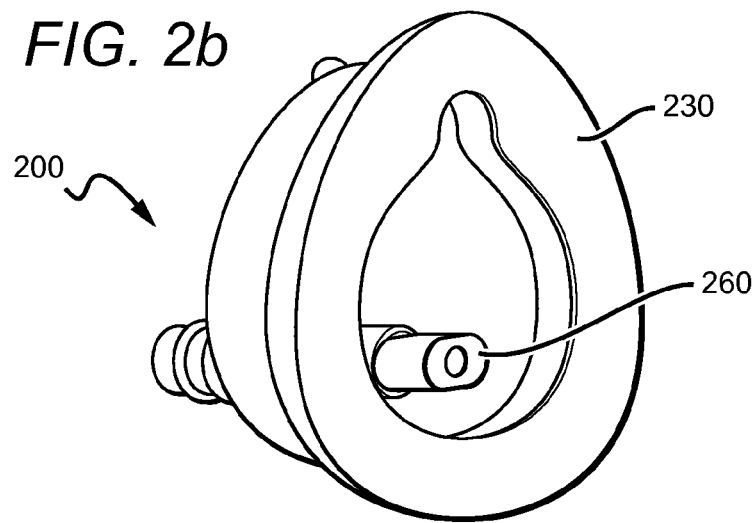
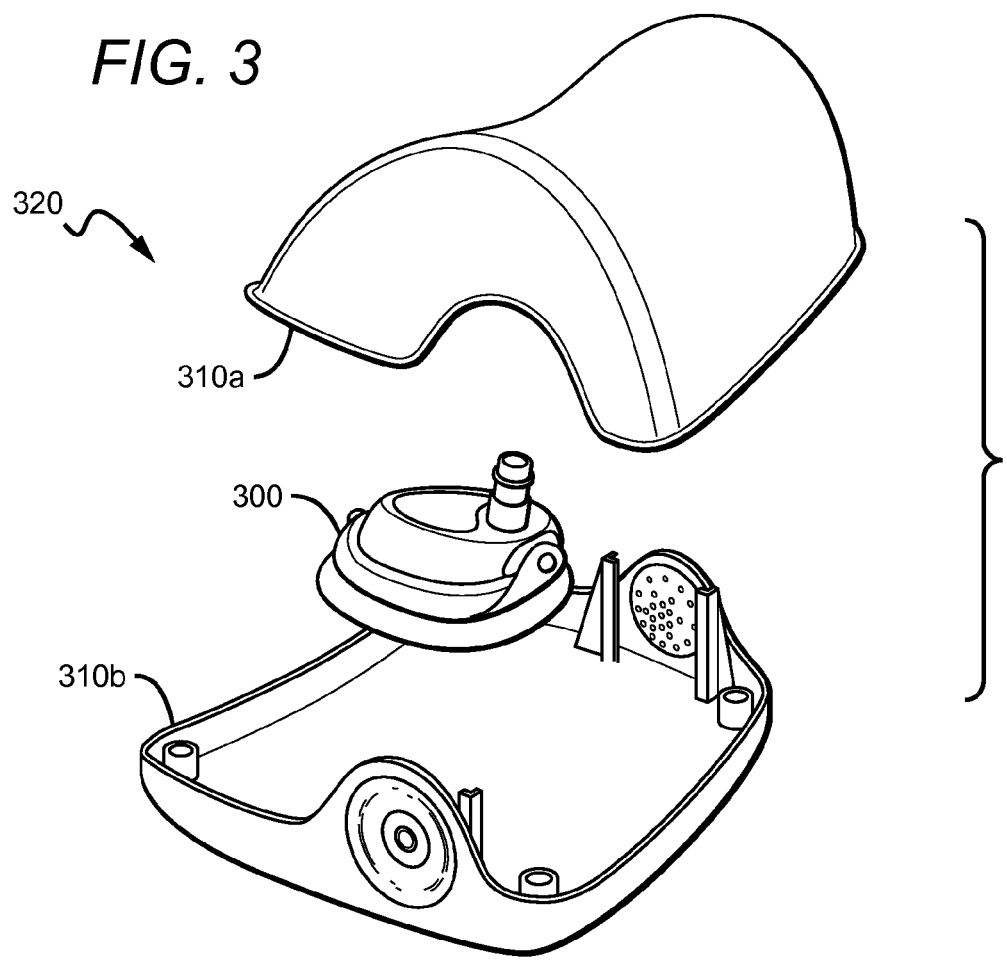

BREATHING MASK WITH STICKY EDGE

This application claims the benefit of priority to U.S. Provisional Application having Ser. No. 60/992,863 filed on Dec. 6, 2007. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is assisted breathing technologies.

BACKGROUND

There are numerous reasons why a victim having breathing problems would require assistance breathing including suffering from sleep apnea, requiring anesthesia during surgery, or having a cardiopulmonary emergency. Previously known breathing assist kits include mask to support assisted breathing. However, such kits can be difficult to use, require specialized training, are bulky, or otherwise unusable by a care provider lacking sufficient training.

One issue with previously known breathing assist kits is that a tube could be required for intubation to ensure a victim's trachea is open to air flow. Intubation is well beyond the skill level of an ordinary person attempting to provide care to the victim. However, not all breathing kits require intubation, but rather include a simple mask to provide air flow while a care provider tilts the victim's head into a proper position. Unfortunately, the care provider again could lack sufficient training to place a victim in a position having proper capital cervical extension for improved air flow.

Another issue with breathing kits is that provided breathing masks have to be strapped to a victim's head to prevent the mask from becoming dislodged. For example, U.S. Patent Application Publication to Lurie et al. 2003/0062040 describes an emergency ventilation system having a strapped mask as is the trend in the market for such systems. Unfortunately, it takes time to put the breathing mask on a victim's face which can cost valuable time especially during a life or death emergency. Additionally, should the victim vomit, the mask should be removed quickly so that the victim's mouth can be cleaned to prevent choking. Furthermore, known masks including those described by Lurie lack features that allow a care provider, especially untrained providers, to determine if the victim's airway is indeed clear.

What has not yet been appreciated is that a strapless mask, counter to current trends in breathing assist kits, can be used in conjunction with a cranio-cervical extension device to overcome the limitations of know kits. Preferably masks also include additional features to view into the mask to allow a care provider to ensure a victim's airway is clear. A strapless mask can be removed quickly in the event the victim is in respiratory distress. U.S. Patent Application Publication 2005/0056286 to Huddart et al. describes respiratory masks that could be strapless. However, Huddart fails to address the need for features to view into the mask or including such a mask with a breathing assist kit.

Thus, there is still a need for providing a breathing assist kit that ensures a victim's air passage is open and that includes a mask that can be easily coupled to a victim's face and or removed if necessary.

SUMMARY OF THE INVENTION

The present invention provides apparatus, systems and methods in which a breathing assist kit can be used to ensure a victim's trachea is open for air flow and that includes a mask which can be quickly put on or taken off of a victim's face. Preferred masks have a window or a light source for viewing into the victim's airway.

A preferred breathing assist kit comprises a cranio-cervical extension device and a strapless breathing mask. When placed beneath a victim's neck, the cranio-cervical extension device properly causes capital extension of the victim's carnio-cervical area to improve air flow into and out of the lungs. The breathing mask couples to the victim's face without requiring straps. In preferred embodiments, the mask comprises a sticky or tacky gasket to prevent the mask from moving from a desired location on the victim's face.

Preferred masks include a light source for illumination the interior of the mask or the interior of the victim's air passage. Contemplated light sources can include a window, a light gathering lens, or electrical lights (e.g., light emitting diodes).

Various objects, features, aspects and advantages of the inventive subject matter will become more apparent from the following detailed description of preferred embodiments, along with the accompanying drawings in which like numerals represent like components.

BRIEF DESCRIPTION OF THE DRAWING

FIG. 1b is a left side perspective view of the cranio-cervical extension device of FIG. 1a.

FIG. 1c is a perspective view of the strapless breathing mask of FIG. 1a.

FIG. 1d is a right side perspective view of the cranio-cervical extension device of FIG. 1a.

FIG. 2b is a back perspective view of the strapless breathing mask of FIG. 2a.

FIG. 3 is an exploded view of the cranio-cervical extension device of FIG. 2a, with a strapless breathing mask disposed in a cavity of the device

DETAILED DESCRIPTION

Figure 1A:
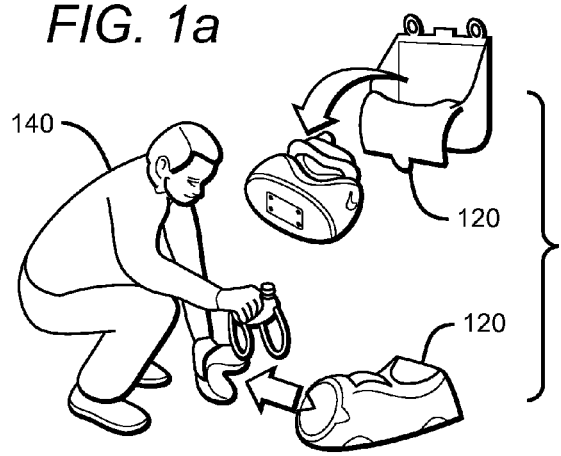
FIG. 1a is a schematic of a breathing assist kit having a cranio-cervical extension device and a strapless breathing mask.
Figure 1B:
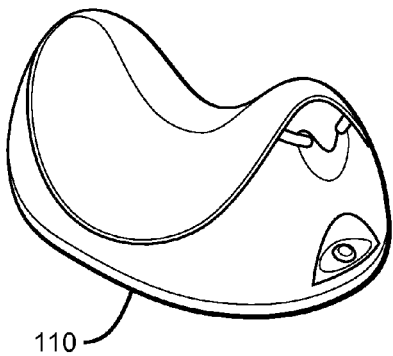
Figure 1C:
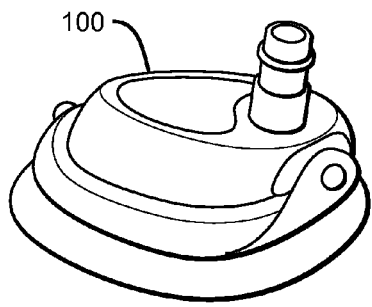
Figure 1D:
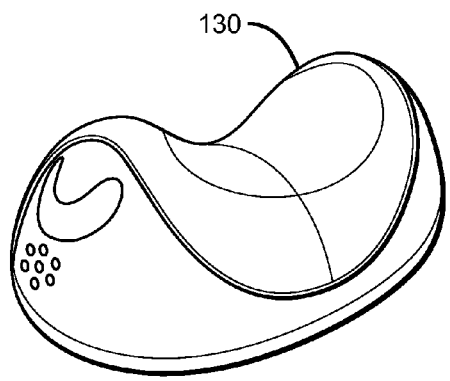

In FIGS. 1a-1d, a breathing assist kit 120 comprises a cranio-cervical extension device 110 and a strapless breathing mask 100. Example device 110 has mask 100 enclosed within a cavity of device 110. Example device 130 illustrates a scenario where provider has removed mask 100 from an interior cavity of device 130.

Kit 120 is preferably configured for emergency use and can be mounted on a wall of a high traffic area where people congregate. For example, an emergency kit 120 can be placed within a school, a mall, a church, an airport, or other areas.

In a preferred embodiment, a cranio-cervical extension device 130 comprises a saddle shaped pillow that cradles the neck and provides proper capital extension for assisted breathing. When the pillow is positioned beneath a victim's neck, the victim's trachea has improved air flow during assisted breathing. Although a preferred kit 120 includes a saddle shaped pillow, all other cranio-cervical extension devices are also contemplated including a wedge that raises the victim's thoracic spine and provides proper capital extension of the victim's carnio-cervical area for improved air flow. An example of a suitable carnio-cervial extension device having a saddle shaped pillow is described in co-owned U.S. patent application having Ser. No. 12/327,363 titled "Cranio-Cervical Extension Pillow with Dual Arcs".

A preferred cranio-cervical extension device 320 also has a cavity that is defined by the shell of the device, as shown in FIG. 3. It is contemplated that the kit's mask 300 is packaged within the cavity to reduce the overall volume of the kit. An example of a suitable carnio-cervial extension device is described in co-owned U.S. Patent Application having Ser. No. 12/327,363 titled "CPR System with Feedback Instructions".

The kit's mask 100 preferably comprises a ventilation mask, a resuscitation mask, or a respiration mask shaped to cover a wide variety of victims' nose and mouth region. However, it is contemplated that mask 100 could also cover only the nose or only the mouth.

Figure 2A:
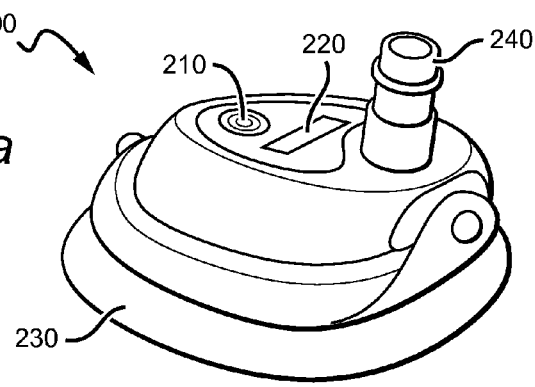
FIG. 2a is a front perspective view of a strapless breathing mask.

In FIGS. 2a and 2b, a strapless breathing mask 200 comprises a seal 230 that couples mask 200 to a victim's face. A preferred breathing mask 200 includes one or more light sources 210 or 220 that provide illumination to the interior of mask 200 or the victim's airways.

Seal 230 associated with strapless mask 200 allows the mask to stay affixed to the victim's face during potentially violent maneuvers including CPR compression strokes. Seal 230 does not necessarily have to be air tight, but rather substantially adheres to the victim's face using a suitable adhesive, preferably a bio-compatible adhesive. Preferably the seal is a sticky or tacky gasket that can be replaced after use. By providing a sticky gasket, the mask can be placed on a victim quickly and removed quickly should a need arise. Examples of suitable hypoallergenic, bio-compatible adhesives include those offered by Polymer Science, Inc. or Dow-Corning comprising silicon gel or polyurethane.

In yet other embodiments mask 200 also includes one or more advantageous features. Preferably mask 200 includes at least one passive light source 210 or 220. Mask 200 can include a window 220 that provides a care provider a clear view into the interior of mask 200 or the victim's airway. This allows the care giver to make sure the airway is unobstructed. Mask 200 can additionally include a light gathering lens 210 to provide additional light within the mask. Especially preferred lenses include a Fresnel lens that both gathers light and magnifies the view within the mask. Lens 210 provides an inexpensive means for passively illuminating the interior of mask 200. However, it is also contemplated that active light sources can also be incorporated mask 200, possibly an electrical light. An example of a cost effective active light source include battery powered light emitting diodes (LEDs). LEDs are compact, have low power usage, and can be integrated easily into mask 200.

Mask 200 can also including a gas port 240 that can couple to a gas source. Port 200 allows air, or other gas, to enter a victim's trachea during assisted breathing. Contemplated gas sources include pressurized containers, gas tanks, pumps, air bags, humans, or other sources of gas. Port 240 is also contemplated to include one or more valves that control the flow of gas into and out of the mask.

It is also contemplated that the mask 200 can include a bite block 260 (see FIG. 2b) or a tongue depressor (not shown) to keep the victim's mouth unobstructed. In preferred embodiments gas port 240 comprises a lumen through which gas can travel through the bite block 260 to the trachea of the victim.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A breathing assist kit comprising:
   a cranio-cervical extension device comprising a pillow having a shape that opens a victim's air passage when the device pillow is disposed under the victim's neck;
   a strapless breathing mask having a gas port, a bite block, a seal, and a lens;
   wherein the gas port has a lumen coupled with a lumen of the bite block;
   wherein the seal provides an adhesive force that is adapted to allow the mask to stay affixed to a user's face during administration of CPR to the user; and
   wherein the lens is configured to gather light and magnify an interior view of the mask for illuminating a user's airway.

2. The kit of claim 1, wherein the pillow is saddle shaped.

3. The kit of claim 1, wherein the cranio-cervical extension device comprises a cavity.

4. The kit of claim 3, wherein the mask is packaged within the cavity.

5. The kit of claim 1, wherein the seal comprises a sticky gasket.

6. The kit of claim 1, wherein the mask covers at least one of a mouth area and a nose area of the victim's face.

7. The kit of claim 1, wherein the lens comprises a Fresnel lens.

8. The kit of claim 1, wherein the strapless mask further includes an electrical light.

9. The kit of claim 8, wherein the electrical light comprises LEDs.

10. The kit of claim 1, further comprising a mesh bag having an interior space that is sized and dimensioned to store the cranio-cervical extension device and the strapless breathing mask.

* * * * *